United States Patent [19]

Cowan et al.

[11] 4,246,173
[45] Jan. 20, 1981

[54] PROCESS FOR PREPARING TETRASELENOFULVALENES, AND CONDUCTIVE SALTS OBTAINED THEREFROM

[75] Inventors: Dwaine O. Cowan; Aaron N. Bloch, both of Baltimore, Md.; Klaus Bechgaard, Lindenborgvej, Denmark

[73] Assignee: The Johns Hopkins University, Baltimore, Md.

[21] Appl. No.: 899,465

[22] Filed: Apr. 24, 1978

Related U.S. Application Data

[63] Continuation of Ser. No. 629,903, Nov. 7, 1975, abandoned.

[51] Int. Cl.³ .................. C07D 421/02; C07C 163/00
[52] U.S. Cl. .............................. 260/239 R; 260/330.3; 260/326.8; 546/197; 546/207; 546/236; 546/248; 549/32; 549/35; 544/106
[58] Field of Search .................................... 260/239 R

[56] References Cited

U.S. PATENT DOCUMENTS 3,233,963  2/1966  Olin ................................. 260/327 M
4,028,346  6/1977  Engler et al. .................... 260/239 R

OTHER PUBLICATIONS

Engler et al., "J.A.C.S.", 96, pp. 7376-7378 (1974).
Corey et al., "Tetrahedron Letters", No. 33, pp. 3201-3204 (1967).
Ferraris et al., Tetrahedron Letters, No. 27, pp. 2553-2556 (1973).
Breslow et al., Multi-Sulfur and Sulfur and Oxygen Five and Six-Membered Heterocycles, Interscience (1966), p. 544.

*Primary Examiner*—Donald G. Daus
*Assistant Examiner*—D. B. Springer
*Attorney, Agent, or Firm*—Cushman, Darby & Cushman

[57] ABSTRACT

A multistep process for preparing tetraselenofulvalenes involving the synthesis of 1,3-diselenole-2-selones and -2-thiones from diselenocarbamates and α-haloketones followed by coupling of the selone or thione using a dechalkogenizing reagent. New highly conductive salts obtained by coupling certain tetraselenofulvalenes with acceptor compounds are also disclosed.

5 Claims, 2 Drawing Figures

PROCESS FOR PREPARING TETRASELENOFULVALENES, AND CONDUCTIVE SALTS OBTAINED THEREFROM

This is a continuation of application Ser. No. 629,903 filed Nov. 7, 1975, now abandoned.

BACKGROUND OF THE INVENTION

A. Field of the Invention

The present invention relates to a new and improved method of preparing tetraselenofulvalenes and to certain highly electrically conductive organic compounds made by coupling the tetraselenofulvalenes with an electron acceptor.

B. Related Application

Copending U.S. application Ser. No. 440,221 filed by D. O. Cowan and A. N. Bloch now abandoned discloses certain highly electrically conductive organic salts obtained by reacting together an electron donor, e.g. tetrathiofulvalene (TTF) and an electron acceptor such as tetracyano-p-quinodimethane (TCNQ). The salt obtained, using TTF and TCNQ as reactants for purposes of illustration, is called tetrathiofulvalenium-tetracyano-p-quinodimethanide or, more conveniently, $TTF^+$-$TCNQ^-$. This product is comprised of separate homologous columnar stacks of cations and anions, $TTF^+$ being the cation and $TCNQ^-$, the anion. The stacks of radical cations and radical anions in the crystal structure of the product provide a pseudo one-dimensional network for electrical conduction which is an important characteristic of the compounds described in Ser. No. 440,221. Other characteristics of these products include the following:

(a) Both the cation and anion are "open shell", i.e., both have a density of unpaired electrons, which may be fractional. This is an important feature because, if either cation or anion (or both) are not "open shell", lower electrical conductivities result.

(b) Both the cation and anion have a high degree of symmetry. A lack of symmetry can result in electron localization and lower electrical conductivities.

(c) The cation and anion are polarizable and thus reduce electron-electron repulsions.

(d) The compounds from which the salt is made must have at least two "easily available" oxidation states, the transfer of electrons requiring as little energy as possible. Thus, the reduction potential of the anion and the oxidation potential of the cation are low and are as close together as possible, the anion being a good electron acceptor and the cation being a good electron donor.

(e) The molecular charge densities are inhomogeneous and thus facilitate stacking.

The highly electrically conductive salts of Ser. No. 440,221 may be generically described as compounds of the formula $(D^{+n})_x (A^{-m})_y$ wherein $D^{+n}$ is a radical cation and $A^{-m}$ is a radical anion, $+n$ is the formal positive charge on the cation D, x is the number of cation species present, $-m$ is the total negative charge on the anion A, and y is the number of anion species present, the absolute values of the respective products $(+n)(x)$ and $(-m)(y)$ being equal, and wherein D and A are highly symmetric and highly polarizable, and, respectively, have oxidation potentials and reduction potentials which are low and relatively close in absolute value, D and A being present in segregated columnar stacks in the compound, thereby making the compound essentially one-dimensional in nature.

The cation D is more specifically defined in Ser. No. 440,221 as being formed from a member of the group consisting of compounds of the formula

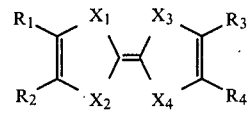

I wherein
$X_1=X_2=X_3=X_4=$ S, Se, or Te;
$X_1=X_4=$ S, $X_2=X_3=$ Se or Te;
$X_1=X_3=$ S, $X_2=X_4=$ Se or Te;
$X_1=X_2=$ S, $X_3=X_4=$ Se or Te;
$R_1=R_2=R_3=R_4=$ H;
$R_1=R_2=R_3=R_4=$ CH$_3$;
$R_1=R_4=$ H, $R_2=R_3=$ CH$_3$;
$R_1=R_3=$ H, $R_2=R_4=$ CH$_3$;
$R_1=R_2=$ H, $R_3$, $R_4$, $=$ CH$_3$;
$R_1=R_2=R_3=R_4=$ CF$_3$;
$R_1=R_2=R_3=R_4=$ —CN;
$R_1=R_2=R_3=R_4=$ —COOH;
$R_1=R_4=$ H; $R_2=R_3=\phi$; and,
$R_1=R_3=$ H; $R_2=R_4=\phi$.

TTF is a compound, or electron donor, according to Formula I above, wherein $X_1$–$X_4$ are each S and $R_1$–$R_4$ are each hydrogen. Thus, TTF may be shown structurally as follows:

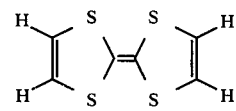

The anion A may be formed from a variety of different electron acceptors. Preferably, however, the anion is derived from TCNQ which may be structurally represented as follows:

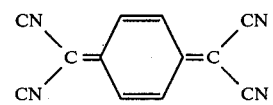

The disclosure of Ser. No. 440,221 is incorporated herein by reference.

DESCRIPTION OF THE PRIOR ART

Research in the field of high conductivity organic compounds has been extensive and intensively pursued in recent years. Early work included that of Acker and Blomstrom (U.S. Pat. No. 3,162,641) wherein charge-transfer compounds of TCNQ and the alkyl-substituted TCNQ's with Lewis bases were formulated. These compounds were unusual in a variety of ways unrelated to their electrical properties but did exhibit increased electrical conductivity (or lowered resistivities) relative to the "electrical insulator" class of organic compounds. Stable radical anion salts were thus produced and were refined by others such that organic salts of TCNQ having room temperature conductivities on the order of $10^2$ ohm$^{-1}$ cm$^{-1}$ were produced.

The invention described in Ser. No. 440,221 provides structurally stable organic compounds having electrical conductivities comparable to those of common metals. In the crystalline form, these compounds are comprised of separate homologous columnar stacks of radical cations and radical anions, both the cation and the anion having a density of unpaired electrons and also having a high degree of symmetry. The electrical conductivity at room temperature of one of the preferred compounds, the radical-cation, radical-anion salt of tetrathiofulvalene (TTF) and tetracyano-p-quinodimethane (TCNQ), is 650 ohm$^{-1}$ cm$^{-1}$, appreciably higher than has previously been found in organic compounds, and $1.4 \times 10^4$ ohm$^{-1}$ cm$^{-1}$ at about 65° C.

Work in this field by ourselves and others is referred to in our paper entitled "Synthesis of the Organic conductor Tetramethyltetraselenofulvalenium 7,7,8,8-Tetracyano-p-quinodimethanide (TMTSF-TCNQ) [4,4′,5,5′-Tetramethyl-$\Delta^{2,2'}$-bis-1,3-diselenolium 3,6-Bis-(dicyanomethylene)cyclohexadienide]" in Journal of The Chemical Society Chemical Communications 1974, dated Nov. 20, 1974 and in papers by ourselves and others submitted recently to Physics Review letters and Journal Organic Chemistry entitled, respectively, "Low-Temperature Metallic Behavior and Resistance Minimum in a New Quasi-One-Dimensional Organic Conductor" and "The Synthesis of 1,3-Diselenole-2-Selones and -2-Thiones". These papers also disclose certain aspects of the present invention as described below.

SUMMARY OF THE INVENTION

In one of its aspects, the present invention provides a novel and effective method for the synthesis of tetraselenofulvalenes, e.g. compounds of formula I above wherein $X_1$–$X_4$ are each selenium, which are themselves useful in preparing highly conductive organic salts by reaction with, for example, TCNQ.

The invention also contemplates certain new and useful highly conductive salts made by reacting tetraselenofulvalenes, notably tetramethyltetraselenofulvalene (TMTSF) or hexamethylenetetraselenofulvalene (HMTSF) with TCNQ or with 11,11,12,12-tetracyano-2,6-naphthoquinodimethane (TNAP).

The objects of the invention, therefore, include the provision of a novel method for preparing tetraselenofulvenes and the use of certain of these tetraselenofulvenes for reaction with TCNQ or TNAP to provide new highly conductive salts of especially unique characteristics. Other objects will also be evident from the following more detailed description of the invention.

DESCRIPTION OF PREFERRED EMBODIMENTS OF THE INVENTION

Figure 1:
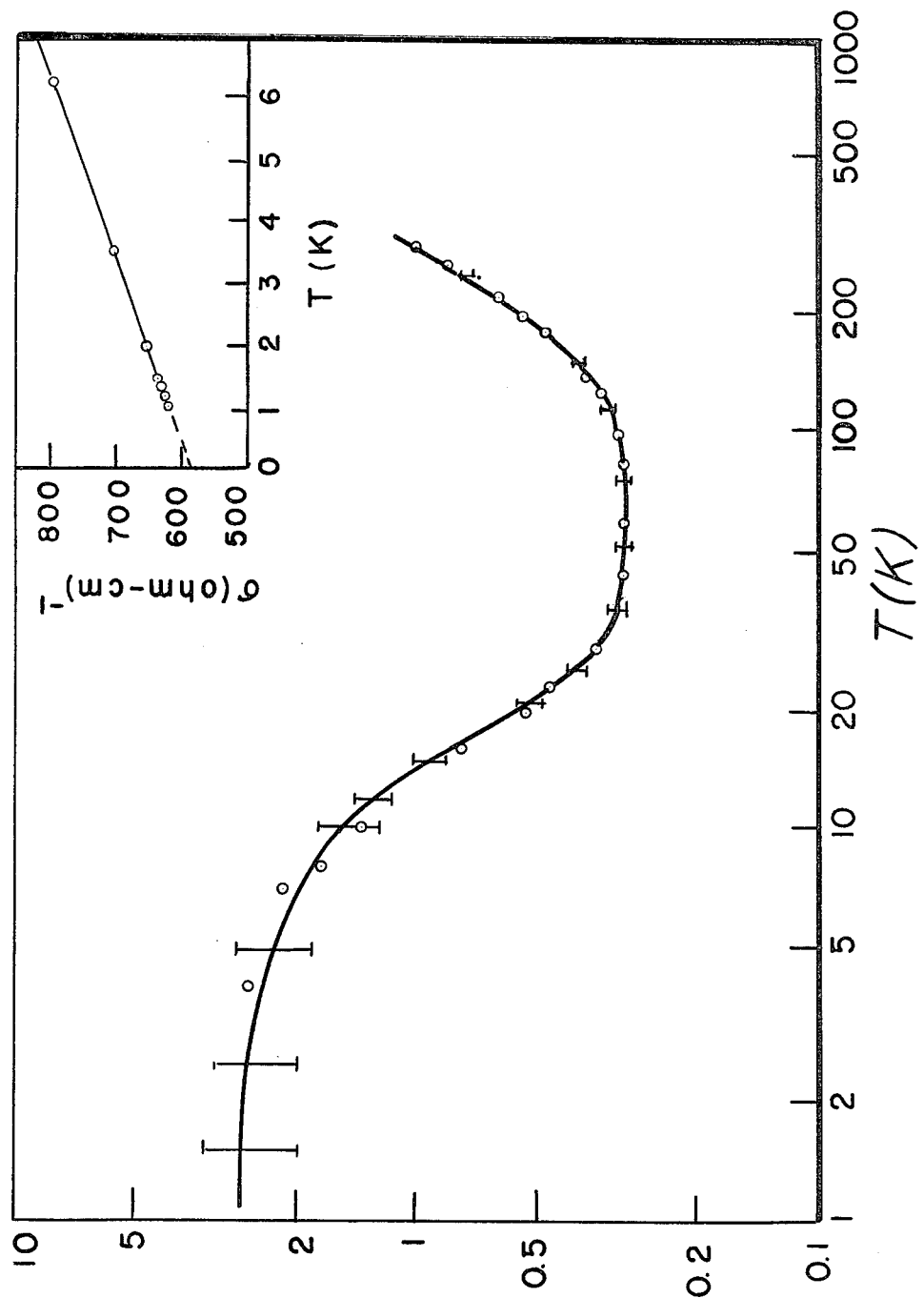
FIGS. 1 and 2 show test results with respect to conductivity and thermoelectric power for a highly conductive salt (HMTSF-TCNQ) according to the invention.

The method of preparing tetraselenofulvenes, according to the invention, comprises a three-step synthesis of 1,3-diselenole-2-selones (or -2-thiones) starting with a diselenocarbamate and an α-haloketone followed by coupling of the selone (or thione) using a dechalkogenizing reagent.

The method of the invention can be used to prepare any tetraselenofulvalene by appropriate selection of the starting materials. Thus, for example, the tetraselenofulvalenes encompassed by Formula I above, whether unsubstituted ($R_1$–$R_4$=H) or substituted ($R_1$–$R_4$=methyl or other lower alkyl, phenyl, etc.) may be prepared by the method of the present invention. Two preferred tetraselenofulvenes which may be prepared by the present method are tetramethyltetraselenofulvalene (TMTSF) and hexamethylene-tetraselenofulvalen (HMTSF). These two tetraselenofulvalenes may be structurally shown as follows:

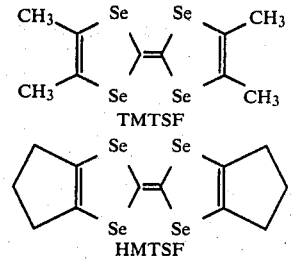

The following reaction scheme illustrates the present method using the preparation of TMTSF for purposes of illustration:

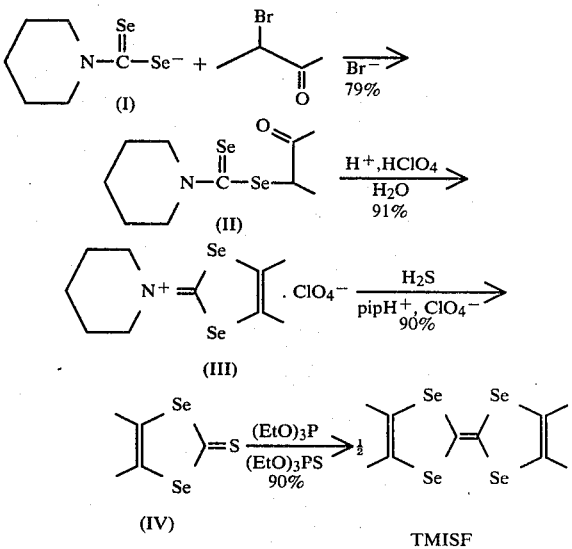

As will be evident, the method illustrated above comprises:

(1) reacting a diselenocarbamate (I) with an α-haloketone to form the product (II);

(2) ring closing the product (II) to give the diseleno compound (III);

(3) converting the ring closed product (III) of step (2) to a thione (IV) or the corresponding selone; and then (4) treating the thione (IV) or corresponding selone with a dechalkogenizing agent, e.g. triethyl phosphite, to give TMTSF.

Typically, in the preparation of TMTSF according to the reaction scheme given above, compound (II) is prepared from piperidinium N,N-pentamethylene diselenocarbamate (I) and excess bromobutanone in dry $CH_2Cl_2$ and ring closure (III) is affected by dissolving (II) in conc. $H_2SO_4$. The resulting compound (III) may be treated with $H_2S$ in neutral or weakly acidic media to form the yellow thione (IV). Treatment of the thione (IV) or the corresponding selone with excess triethyl phosphite gives TMTSF as violet needles, m.p. >250° C. (decomp.); $\nu$max 32,3000 and 19,700 cm$^{-1}$ (log $\epsilon$4.1 and 2.3) TMTSF is more difficult to oxidize than the corresponding sulphur compound, the difference in halfwave potentials of the first oxidation wave being 0.167 V in $CH_2Cl_2$. This means that TCNQ cannot oxidize TMTSF to an appreciable extent in $CH_2Cl$ or MeCN.

Ir will be appreciated that various modifications in terms of reactants and reaction conditions may be made in the method as exemplified above. Thus, while piperidinium N,N-pentamethylenediseleno-carbamate is mentioned as a starting material in the foregoing illustration, other similar diseleno carbamates, e.g. the morpholine and pyrrolidine analogs of piperidinium N,N-pentamethylenediselenocarbamate, may be used as well. However, piperidinium N,N-pentamethylenediseleno carbamate is generally preferred because it is readily obtained and relatively stable.

Any α-haloketone of the formula

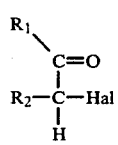

where $R_1$ and $R_2$ are hydrogen, $CH_3$ or other lower alkyl or phenyl or together complete a carbocyclic ring and Hal is a halogen such as chlorine or bromine may be used for present purposes, it being understood that the haloketone should be selected to give the desired $R_1$ and $R_2$ substituents in the final tetraseleno-fulvalene product. Thus, while the preparation referred to above utilizes 3-bromo-2-butanone, other 3-halo-2-butanones, e.g. 3-chloro-2-butanone, or the like, may be used. Preferably the haloketone is used in excess (e.g. 5–25% excess or more).

The reaction between the diselenocarbamate and haloketone involves nucleophilic substitution of a halogen with the N,N-pentamethylene diseleno carbamate anion. This substitution proceeds rapidly at room temperature (20°–25° C.) although the reaction mixture is usually left for a few hours (e.g. 2–4) at this temperature to assure complete reaction. Other temperatures may be used although room temperature is more convenient and generally preferred. It is also preferred to use dry $CH_2Cl_2$ as solvent although other dry inert organic solvents may be used.

The product obtained in the first step is an oxo ester (II) of the formula

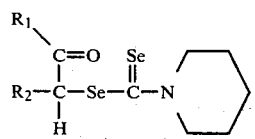

(II)

The product is usually a crystalline, colorless solid which can be recrystallized from nonpolar solvents.

Ring closure of the oxo ester (II) involves the removal of water to form the product (III). Advantageously the ring closure is effected by adding the oxo ester (II) to concentrated sulfuric acid (e.g. 90–98%). This forms the hydrosulfate salt of the ring closed product (2-immonio-1,3-diselenole) which is advantageously converted to the perchlorate or to the fluoroborate by treating the reaction mixture with excess perchloric or fluoroboric acid. The perchlorate salts appear to be the most readily isolated but it is advisable to handle these salts carefully and in small quantity to minimize the possibility of detonation. The salts are normally colorless crystalline solids but may also be pink due to the presence of a small amount of free selenium, which can be removed by dissolving the salts in a solvent, e.g. acetonitrile, filtering and precipitating with ether.

Cleavage of the diselenole (III) obtained in the second step of the present method to form a 1,3-diselenole-2-selone (IV) or 1,3-diselenole-2-thione (IV¹) is advantageously carried out using excess $H_2Se$ or $H_2S$ in methanol or methanol-water mixtures. The reaction, using the diselenole in the form of its perchlorate salt, is illustrated below, it being understood that the product will be a 2-selone or 2-thione depending on whether or not $H_2Se$ or $H_2S$, respectively, is used.

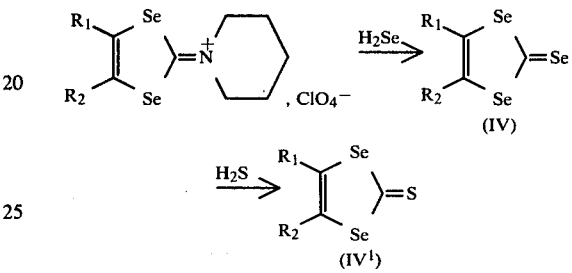

The nature of the solvent used and other reaction conditions, e.g. whether or not a catalyst is used, will vary depending on the diselenole utilized. For example, those perchlorates which are only slightly soluble (e.g. those wherein $R_1=R_2=Ph$) may be usefully suspended in methanol and a basic catalyst (e.g. pyridine in equimolar amount) may be added to effect cleavage. Other more soluble perchlorates are preferably treated with excess $H_2S$ or $H_2Se$ in methanol or methanol-water (e.g. 70% methanol-water) in the absence of a catalyst since certain catalysts, e.g. pyridine and $NaHCO_3$ may tend to produce polymeric tars instead of the desired selones or thiones.

The 1,3-diselenole-2-selones (IV) are red crystalline solids, whereas the -2-thiones (IV¹) are yellow. IR spectroscopy is conveniently used for the identification of these compounds since they both exhibit a very characteristic pattern of two strong (absorption) bands in the 700–1100 cm$^{-1}$ region which arise from the Se—C-Se—Se or Se—CS—Se grouping. The high-frequency bands are found at 880–920 cm$^{-1}$ for (IV) and at 920–1020 cm$^{-1}$ for (IV¹) and has been approximately ascribed to C=Se or C=S stretching vibration, respectively. The low-frequency band is found at 750–780 cm$^{-1}$ for both sets of compounds and is approximately described as a C—Se stretching band.

With regard to UV-Vis spectra, 1,3-diselenole-2-selone has a maximum at 555 nm. Aliphatic substitution has only a minor effect, whereas aryl-substituted compounds exhibit a shift to higher energy. Analogous 2-thiones exhibit a band at approximately 450 nm.

In the final step of the present method, the selones and thiones (IV and IV¹) are coupled by treatment with, for example, triphenylphosphite or a trialkyl-phosphite (typically trimethylphosphite), to give tetraselenofulvalenes in moderate to good yields. The reaction involved is shown above but may be shown more fully as follows:

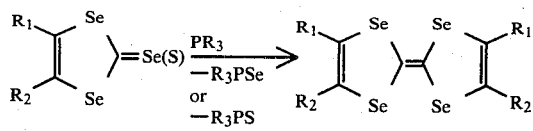

wherein $R^3$ is lower alkoxy, e.g. ethoxy, or phenoxy.

The selones and thiones (IV and IV$^1$) may also be reacted in various other ways to make additional useful products. For example, they may be treated with excess methyliodide to give methiodides according to the following reaction:

the solvent evaporated in vacuo. The resulting yellow oil was recrystallized from hexane to yield slightly yellow crystals of the product IIb having the structure and properties shown in Table I below.

EXAMPLE 2

Example 1 was repeated except that the 3-bromo-2-butanone was replaced by chloroacetone to give the oxo ester (IIa) having the properties shown in the Table I.

EXAMPLE 3

Example 1 was repeated except that the 3-bromo-2-butanone was replaced by phenacylbromide and 2-bromo-1,2-diphenylethanone, respectively, the resulting oxo esters (IIc and IId) being recrystallized from cyclohexane. Characteristics of the ester products are given in Table I.

TABLE I (2-oxo-alkyl)-N,N-pentamethylenediselenocarbamates

| | | | | | NMR$^a$, δ ppm (rel to TMS) | | | |
|---|---|---|---|---|---|---|---|---|
| Symbol | $R_1$ | $R_2$ | Mp °C. | Yield % | $R_1$ | $R_2$, —Se—CH— | —N(CH$_2$—/CH$_2$—) | H$_2$C(CH$_2$-/CH$_2$-) |
| IIa | CH$_3$ | H | 45–46 | 83 | 2.40(3H) | 4.45(2H) | 3.9 and 4.45(4H) | 1.69(6H) |
| | | | | | | J = 7Hz | | |
| IIb | CH$_3$ | CH$_3$ | 43–44 | 79 | 2.31(3H) | 1.47(3H), 4.94(1H) | 4.07(4H) | 1.69(6H) |
| IIc | Ph | H | 99–102 | 95 | 7.4–8.25(5H) | 5.06(2H) | 3.9 and 4.45(4H) | 1.75(6H) |
| IId | Ph | Ph | — | 15 | —$^b$ | — | — | — |

$^a$CDCl$_3$
$^b$not recorded

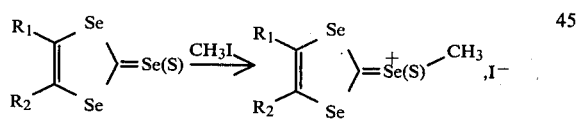

The thiones may also be used to prepare 1,3-dithiolium salts by peracid oxidation. However, the corresponding 1,3-diselenolium salts cannot apparently be prepared by this method, probably because of oxidation of the selenium atoms in the ring.

The following examples illustrate the various steps of the method of the present invention:

Step 1: Preparation of (2-oxo-alkyl)-N,N-pentamethylenediselenocarbamates

EXAMPLE 1

Piperidinium-N,N-pentamethylenediselenocarbamate (0.03 mol) dissolved in 60 ml dry CH$_2$Cl$_2$ was added, under argon, to a stirred solution of 3-bromo-2-butanone (0.04 mol) in 200 ml dry CH$_2$Cl$_2$. After the addition was completed, the solution was left with stirring at room temperature for 4 hours, and then washed with five 100 ml portions of water, dried over MgSO$_4$ and

Step 2: Preparation of 2-(N,N-pentamethyleneimino)-1,3-diselenolium Salts

EXAMPLE 4

The product IIb (0.003 mol) was dissolved slowly in 3 g conc. H$_2$SO$_4$. After standing ½ hour at room temperature enough EtOAc was added cautiously to start precipitation of the hydrosulfate. The solution was then filtered into a mixture of 1–2 ml 70% HClO$_4$ and 50 ml abs EtOH, and 300–500 ml ether added. The resulting white solid was filtered off, washed with ether and dried in vacuo to give the product IIIb of the structure and properties shown in Table II.

EXAMPLES 5–7

Example 4 was repeated using the appropriate oxo ester obtained according to Examples 2–3. The structures and other characteristics of the resulting products IIIa, IIIc and IIId are shown in Table II.

TABLE II

2-N,N-pentamethyleneimino-1,3-diselenolium-perchlorates $$\begin{array}{c} R_1 \\ \diagdown \\ R_2 \end{array} \begin{array}{c} Se \\ \diagup \\ Se \end{array} \Big\rangle = \overset{+}{N} \Big\langle \begin{array}{c} \\ \end{array} \Big\rangle , ClO_4^- \quad (III)$$

| Symbol | $R_1$ | $R_2$ | Yield % | NMR, δ (rel. to TMS) $R_1$ | $R_2$ | $=\overset{+}{N}\diagup^{CH_2-}_{CH_2-}\diagdown^{-CH_2}_{-CH_2}\diagup CH_2$ | |
|---|---|---|---|---|---|---|---|
| | | | | J = 1.5Hz | | | |
| IIIa | H | $CH_3$ | 87 | 7.83(1H) | 2.54(3H)[a] | 3.97(4H) | 1.8–2.15(6H) |
| IIIb | $CH_3$ | $CH_3$ | 91 | 2.66(6H)[b] | | 3.66(4H) | 1.7–2.1(6H) |
| IIIc | H | Ph | 91 | 7.89(1H) | 7.59(5H)[c] | 3.90(4H) | 1.8–2.15(6H) |
| IIId | Ph | Ph | 90 | — | — | — | — |

[a] $(CD_3)_2CO$
[b] $CD_3CN$
[c] $CF_3COOH$

Step 3: Preparation of 1,3-diselenole-2-selones or -2-thiones

EXAMPLE 8

The product IIIb (0.0025 mol) was dissolved in 60 ml 70% MeOH-water cooled to −10° C., and the stirred solution, which was kept under argon, was treated with a sixfold excess of $H_2Se$. A red solid was slowly formed and the solution was allowed to warm to 0° C. over 2-3 hours. 40 ml of water was added and the solid filtered off and dried in a desiccator over $P_2O_5$. Recrystallization from heptane yielded bright red plates of the product IVb. Structure and other characteristics of IVb are shown below in Table III.

EXAMPLE 9

Example 8 was repeated using IIIa in lieu of IIIb. The resulting product IVa is further identified by structure and other characteristics in Table III.

EXAMPLES 10-11

Example 8 was repeated using IIIc and IIId in lieu of IIIb. Additionally, because of the insolubility of IIIc and IIId, they were suspended in absolute MeOH and an equimolar amount of pyridine was added as a catalyst. The products IVc and IVd, respectively, were recrystallized from absolute EtOH and are further described in Table III.

EXAMPLES 12-13

Examples 8 and 9 were repeated but using $H_2S$ instead of $H_2Se$ to give the corresponding thione products ($IV^1b$) and ($IV^1a$), respectively, having the structure and characteristics shown in Table III. Due to its lower reactivity, however, the $H_2S$ was passed through the stirred solution at room temperature for 4-6 hours.

TABLE III

1,3-diselenole-2-selones and -2-thiones, $$\begin{array}{c} R_1 \\ \diagdown \\ R_2 \end{array} \begin{array}{c} Se \\ \diagup \\ Se \end{array} \Big\rangle = Se \quad (IV) \quad \text{and} \quad \begin{array}{c} R_1 \\ \diagdown \\ R_2 \end{array} \begin{array}{c} Se \\ \diagup \\ Se \end{array} \Big\rangle = S \quad (IV^1)$$

| Symbol | $R_1$ | $R_2$ | Yield, % | Mp °C. | IR $cm^{-1,a}$ | UV-VIS, nm $(\epsilon)^b$ | $NMR^d$ δ ppm |
|---|---|---|---|---|---|---|---|
| IVa | $CH_3$ | H | 66 | 80–81 | 890,880 and 700 | 558(197),417(15,500) 318(870),266(7,300) | 2.42(3H); 7.43(1H), J = 1.5 Hz |
| IVb | $CH_3$ | $CH_3$ | 60 | 149–150 | 890, and 762 | 555(224),424(14,800) 328(730),266(6,200) | 2.25 |
| IVc | Ph | H | 86 | 121–122 | 902,885 and 732 | [c]524(296),431(16,800) | 7.36(5H), 7.87(1H) |
| IVd | Ph | Ph | 55 | 161–63 | 902,889 and 750 | [c]528(291), 434(19,300) | 7.15 |
| $IV^1a$ | $CH_3$ | H | 90 | 81–81.5 | 1020,990 and 752 | 460(sh),382(15,000) 295(1,400),255(9,800) | 2.42(3H), 7.23(1H) J = 1.5 Hz |
| $IV^1b$ | $CH_3$ | $CH_3$ | 87 | 101–102 | 1020, and 772 | 453(53),385(13,800) 304(1,000),276(2,400) 254(8,300) | 2.19 |

[a] KBr
[b] hexane
[c] $CH_2Cl_2$
[d] $CDCl$, rel. 7MS

Step 4: Preparation of Tetraselenofulvalenes

EXAMPLE 14

One part of the selone product of Example 8 (IVb—i.e. $R_1=R_2=CH_3$) was suspended in acetonitrile and stirred with excess triethyl phosphite (30% concentration) at room temperature (20°–25° C.) with the precipitation of TMTSF needles. Recrystallization from acetonitrile gave violet needles in good yield, m.p. >250° C. (decomp.); $v_{max}$ 32,3000 and 19,700 $cm^{-1}$ (log $\epsilon$4.1 and 2.3).

EXAMPLE 15

Example 14 was repeated except that the thione of Example 12 is used to give a product essentially identical with that obtained in Example 14.

EXAMPLE 16

Example 14 is repeated except that the selone is

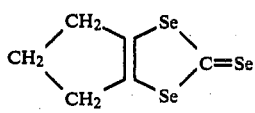

to give HMTSF as the product.

The selone used in this example can be prepared by the method described in the foregoing examples using

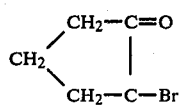

as the α-haloketone.

Fundamental to the success of the present method, as illustrated above, is the three-step synthesis of the selone or thione from a diselenocarbamate and α-haloketone.

Engler and Patel (J. Amer. Chem. Soc. 96, pages 7376–7378, 1974) have previously proposed the preparation of unsubstituted 1,3-diselenole-2-selone from sodium acetylide, selenium and carbon diselenide using a modification of a procedure originally developed to prepare 1,3-dithiole-2-thiones (R. Mayer and B. Gebhardt, Chem. Ber., 97, 1298 (1964) and R. Mayer and A. K. Müller, Z. Chem., 4, 384 (1964)). The method of the present invention provides a more convenient pathway to the mono- and disubstituted 1,3-diselenole-2-selones and -2-thiones. Thus, for example, when compared to the Engler and Patel procedures, the present method offers the advantage that 4,5-disubstituted 1,3-diselenoles are obtainable, since no acetylenic hydrogen is required.

Preparation of Organic Conductor Salts

Tetraselenofulvalenes, as noted above, can be used as the donor compound in the preparation of highly conducting organic "metals" of the following general type:

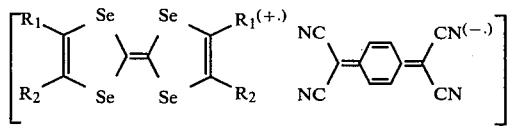

As described in Ser. No. 440,221, these conductive organic compounds may be prepared by mixing together equimolar amounts of the donor component and, for example, TCNQ or like acceptor component in hot acetonitrile or other solvent followed by cooling to crystallize out the conductive salt.

According to another aspect of the invention, it has been found that certain new highly conductive salts of this type have particularly unique and useful conductivity properties. These novel salts are those obtained by coupling TMTSF or HMTSF with TCNQ or TNAP (11, 11, 12, 12 tetracyano-2,6-naphthoquino-dimethane). These new salts may be prepared in the manner described in Ser. No. 440,221 and, for convenience, may be identified as:

(TMTSF)+-(TCNQ)−
(TMTSF)+-(TNAP)−
(HMTSF)+-(TCNQ)−
(HMTSF)+-(TNAP)−

Preparation of the conductor TMTSF—TCNQ [4,4',5,5'-tetramethyl-$\Delta^{2,2'}$-bis-1,3-diselenolium 3,6-bis-(dicyanomethylene)cyclohexadienide] is shown in the following example:

EXAMPLE 17

Equimolar amounts of TMTSF and TCNQ were dissolved in hot $CH_2Cl_2$ or MeCN followed by cooling to precipitate out TMTSF-TCNQ crystals. Two forms of crystals were observed, one a coppery red insulator with a room temperature d.c. conductivity of $10^{-5}\Omega^{-1}$ cm$^{-1}$ and the other a black organic "metal" with a room temperature d.c. and microwave conductivity of at least $800\Omega^{-1}$ cm$^{-1}$ comparable to the best organic conductors.

The other conductor salts of the invention can be prepared in similar fashion using the appropriate donor and acceptor components. The desired coupling may also be conducted in other ways, for example, by diffusion of the reactants in H-shaped tubes.

Figure 2:
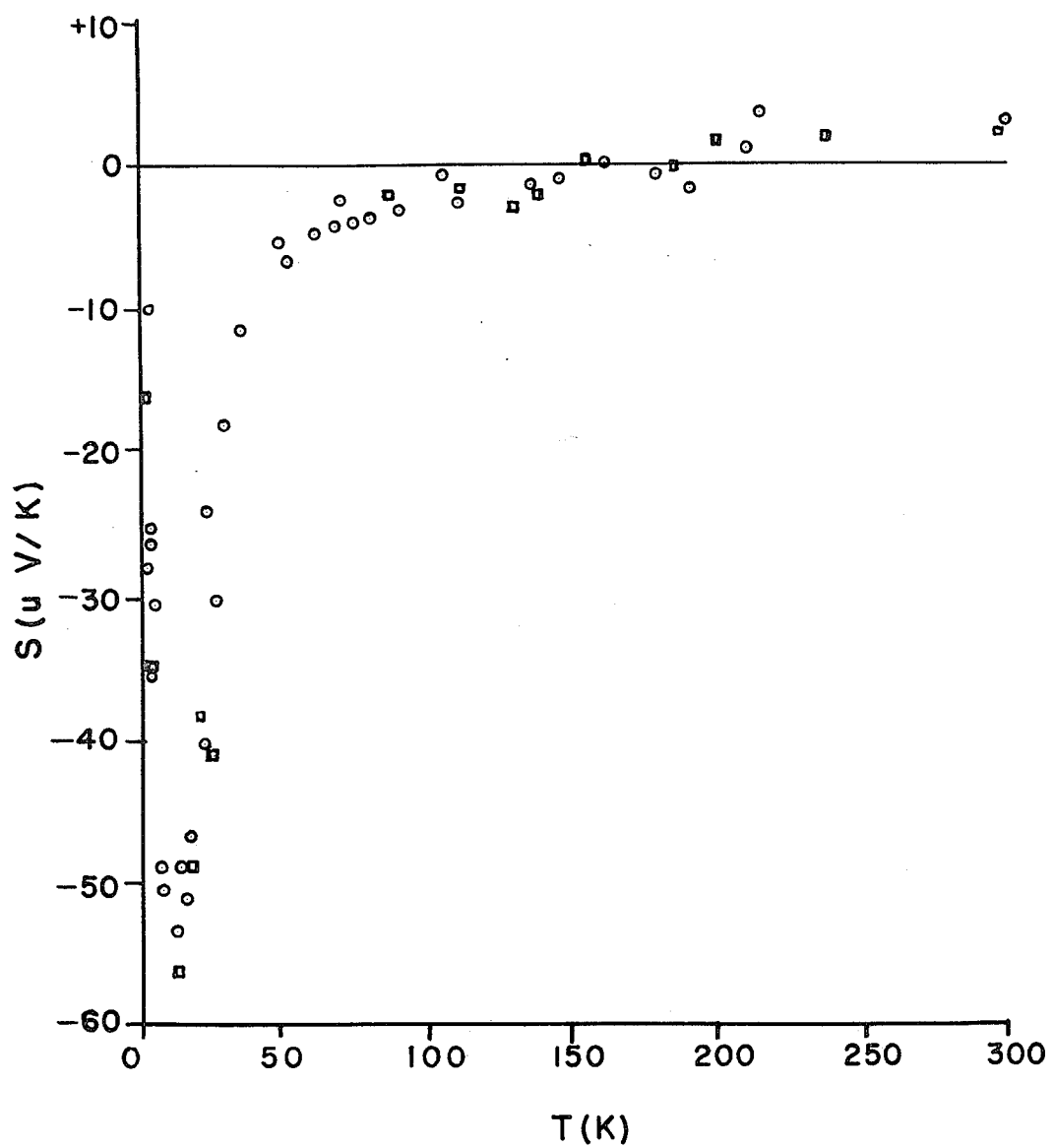

FIGS. 1 and 2 show certain properties of the salt HMTSF-TCNQ. In particular, FIG. 1 shows normalized d.c. (solid line) and microwave (*) resistivities of HMTSF-TCNQ. Error bars represent standard deviations among nine d.c. crystals. The inset in FIG. 1 shows the d.c. conductivity of a typical HMTSF-TCNQ crystal extrapolated to T=0.

FIG. 2 exemplifies the absolute thermoelectric power of HMTSF-TCNQ. Data point symbols distinguish warming and cooling runs for two crystals.

FIGS. 1 and 2 are considered more fully below.

The salt HMTSF-TCNQ is a quasi-one-dimensional conductor on the lines of the compound TTF-TCNQ described in Ser. No. 440,221. However, HMTSF-TCNQ appears to be unique in behaving as a metal throughout the temperature range 1.1–300 K. Electronically, the donor molecule HMTSF is indistinguishable from its tetramethyl analog, TMTSF, whose triclinic TCNQ salt becomes insulating below 70 K. Sterically, however, the larger, non-planar HMTSF is incompatible with the crystal structure of TMTSF-TCNQ. Instead, HMTSF-TCNQ is nearly orthorhombic, with a density of chains per unit area about 20% lower than that of TTF-TCNQ. The structure is disordered along one principal direction perpendicular to the stacking axis. The higher symmetry, reduced interchain coupling, and lack of three-dimensional long-range order suggest natural rationalizations for suppression of the insulating state, although this has not yet been established.

The room temperature d.c. conductivity of HMTSF-TCNQ is the largest of any known organic substance. Measurements range from 1391 to 2178 $\Omega^{-1}$cm$^{-1}$, with no distinction between two separately synthesized crystal batches. This spread is within error in measuring the sample dimensions (typically 23.5×0.04>0.02 mm), correction being made by normalizing the resistivity $\rho(T)$ for each crystal to its room temperature value. The average result for nine typical samples is plotted in FIG.

1, with error bars representing standard deviations at selected temperatures.

With cooling from 300 K, $\rho(T)$ for HMTSF-TCNQ drops rapidly. Below 110 K, however, the curve flattens and passes through a broad minimum between 45 and 75 K, where the conductivity is about 3.4 times its room temperature value. With further cooling the resistivity rises again, but extrapolation from 1.1 K to T=O yields values still in the metallic range. At no temperature has hysteresis in $\rho(T)$ between cooling and warming been observed.

In close agreement with the d.c. results is the normalized microwave resistivity at 10 GHz, presented in FIG. 1 for two additional crystals. The microwave dielectric constant remains large and negative, as for a metal, throughout the temperature range.

The resistivity appears to consist of at least two distinct contributions. Above 100 K, the normalized curves are remarkably reproducible, with standard deviation below 45 K rises to more than 25%, with variations of nearly a factor of four among individual samples. It is presumed that conduction is limited by impurities and lattice defects. The simplest inference is that $\rho(T)$ is everywhere the sum of an intrinsic part which decreases and an "impurity" part which increases as the temperature is lowered, forming the minimum at their crossing point.

By least-squares analysis it is found that with correlation coefficient 0.99996, the intrinsic resistivity of HMTSF-TCNQ above 110 K is described by $$\rho(T)/\rho(300\ K) = a + bT^\nu \tag{1}$$

where a=0.264, b=8.84×10$^{-7}$, and $\nu$=2.39±0.01. Previous studies have shown that the high temperature resistivities of other compounds of this class also obey Equation (1), with =2.33±0.14 (TTF-TCNQ), 2.34±0.04 (TMTTF-TCNQ), and 2.4±0.2 (TMTSF-TCNQ).

From the trend in the coefficient b, which decreases with increasing molecular weight, it is inferred that the second term in Equation (1) is phonon-dominated. For a simple one-dimensional metal above the Debye temperature, the usual one-electron-acoustic phonon interaction leads to a resistivity proportional to T, as observed in (SN)$_x$. It is believed, then, that the large $\nu$ found for the present materials is not a general feature of the one-dimensional metallic state, but rather a peculiarity of the two-band organic systems. It is noted that a strong temperature dependence for the phonon part of the resistivity is expected if the density of electronic states is strongly energy-dependent near the Fermi level, as implied by approximate band-structure calculations, or if low-lying intramolecular optical modes play an important role in the scattering, as suggested by recent spectroscopic results. In any event this contribution should become exponentially small in the low-temperature regime, as the short-wavelength phonons responsible for the resistivity are frozen out.

The strong temperature dependence of the impurity resistance below 45 K is difficult to explain within the single-particle framework. Special energy dependences for the density of states or scattering potential are possible, but unlikely to recur in systems so chemically disparate as metallic (SN)$_x$ and semimetallic HMTSF-TCNQ. On the other hand, Fukuyama et al (Phys. Rev. Lett., 33, 305 (1974) have argued quite generally that the divergence of the electronic polarizability at q=2k$_F$ can lead to a dynamic enhancement of the impurity scattering, and hence the resistivity, of a one-dimensional metal as T→O. An exact calculation affirms this conclusion for a simple model over a certain range of physically reasonable coupling constants. The effect bears a mathematical and experimental resemblance to the Kondo phenomenon.

Within the Born approximation, the theory predicts an inverse power-law dependence of the resistivity on the temperature. Such a law is obeyed by HMTSF-TCNQ with exponent ~1.7, but only over a limited temperature range above 12 K. At low temperatures, the Born approximation must break down as the scattering rate increases. Quantitative estimates are especially difficult for the present narrow-band, semimetallic case, but consistency requires that the higher-order terms limit the enhanced rate so as not to exceed the electronic bandwidth as T→O. In TMTSF-TCNQ, this limit corresponds to $\sigma(O)$=875 $\Omega^{-1}$ cm$^{-1}$ if all the chains are conducting.

A low temperature thermoelectric power roughly proportional to $T^2(\partial\ln\rho/\partial T)$ and nearly independent of impurity concentration is observed for HMTSF-TCNQ. FIG. 2 presents the absolute thermoelectric power S(T) for crystals from two separately synthesized batches of HMTSF-TCNQ. The small, positive, nearly linear high temperature thermopower is typical of selenium analogs of TTF-TCNQ, but the strong negative peak near 16 K [the inflection point in $\ln\rho(T)$] suggests that a different scattering mechanism has emerged. A weaker negative peak has been reported for (SN)$_x$ at low temperatures.

In those quasi-one-dimensional conductors where a metal-to-insulator transition does occur at a finite temperature $T_c$, the divergence of the leading term in the impurity scattering should ariseaas T→$T_c$. In TTF-TCNQ, where $T_c$−54 K, the conductivity maximum, $\sigma_{max}$ usually occurs at $T_{max}$−59 K, but diminishes and moves to higher temperature with decreasing sample quality. Likewise, the weakly disordered sulfur-selenium compound, DSDTF-TCNQ, has a lower $\sigma_{max}$ and higher $T_{max}$ than either of its ordered isostructural analogs TTF-TCNQ and TSF-TCNQ. It is possible, then, that in these materials $\sigma_{max}$ represents a crossing of phonon and enhanced impurity resistance curves as in (SN)$_x$ and HMTSF-TCNQ, and that the region $T_c < T < T_{max}$ is characterized by fluctuation resistivity.

As indicated, HMTSF and TMTSF also form useful conducting salts with the electron acceptor TNAP, the naphtho-analog of TCNQ, and these salts constitute a part of the present invention. D.C. and microwave measurements indicate that both HMTSF-TNAP and TMTSF-TNAP remain metallic to 1.1 K and display resistance minima st somewhat higher temperatures and lower conductivities than HMTSF-TCNQ.

The invention is defined in the following claims wherein:

We claim:

1. An electrically conductive organic salt selected from the group consisting of:
    (1) tetramethyltetraselenofulvalene 7,7,8,8-tetracyano-p-quinodimethanide
    (2) hexamethylenetetraselenofulvalene 7,7,8,8-tetracyano-p-quinodimethanide
    (3) tetramethyltetraselenofulvalene 11,11,12,12-tetracyano-2,6-naphthoquinodimethane
    (4) hexamethylenetetraselenofulvalene 11,11,12,12-tetracyano-2,6-naphthoquinodimethane.

2. An electrically conductive salt according to claim 1, said salt being hexamethylenetetraselenofulvalene 7,7,8,8-tetracyano-p-quinodimethanide.

3. An electrically conductive salt according to claim 1, said salt being hexamethylenetetraselenofulvalene 11,11,12,12-tetracyano-2,6-naphthoquinodimethane.

4. A method of preparing a tetrasubstituted tetraselenofulvalene of the formula

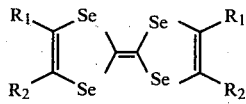

which consists essentially of:
(1) contacting in dry inert organic solvent, a diselenocarbamate of the formula

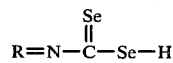

with an α-haloketone of the formula:

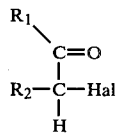

to effect nucleophilic substitution of the halogen atom in said ketone and form a diseleno keto ester of the formula

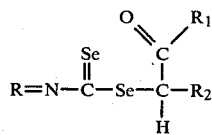

wherein Hal is chlorine or bromine, R represents polymethylene which with the adjacent —N— atom completes a 5- or 6-membered N-heterocyclic ring, one of $R_1$ and $R_2$ is hydrogen, methyl or phenyl and the other is methyl or phenyl, or $R_1$ and $R_2$ together form the alkylene bridging group —CH$_2$CH$_2$CH$_2$—, (2) ring-closing said keto ester by adding the same to concentrated sulfuric acid to form the hydrosulfate salt of the formula:

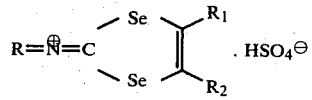

(3) converting the hydrosulfate salt of step (2) to the perchlorate or perfluoroborate by treating the reaction mixture of step (2) with excess perchloric or fluoroboric acid;

(4) converting the perchlorate or perfluoroborate to a selone or thione of the formula:

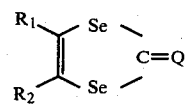

where Q is Se or S by mixing said perchlorate or fluoroborate with excess H$_2$Se or H$_2$S in methanol or methanol-water mixture at −10° C.; and (5) converting said selone or thione to said tetraselenofulvalene by treating the same with an excess of a dechalkogenizing agent selected from the group consisting of triphenyl phosphite, trimethyl phosphite or triethyl phosphite, the products obtained in reaction steps (1), (3) and (4) being separated before the next reaction step.

5. The method of claim 4 wherein piperidinium N,N-pentamethylene-diseleno-carbamate is reacted with α-bromobutanone in step (1) followed by ring-closing the resulting product in concentrated sulfuric acid and converting the ring-closed product to the thione or selone by treatment with H$_2$S or H$_2$Se in neutral or weakly acid media followed by reacting the thione or selone with said phosphite to obtain said tetraselenofulvalene.

* * * * *